United States Patent [19]

Smith

[11] Patent Number: 4,462,914

[45] Date of Patent: Jul. 31, 1984

[54] METHOD OF CONTROLLING CORBICULA

[75] Inventor: Alan L. Smith, Pittsburgh, Pa.

[73] Assignee: Calgon Corporation, Pittsburgh, Pa.

[21] Appl. No.: 455,170

[22] Filed: Jan. 3, 1983

[51] Int. Cl.$^3$ .............................................. C02F 1/68
[52] U.S. Cl. .................................................... 210/755
[58] Field of Search ...................... 210/735, 755, 764; 424/329; 43/124

[56] References Cited

U.S. PATENT DOCUMENTS

| | | | |
|---|---|---|---|
| 3,461,163 | 8/1969 | Boothe | 210/735 |
| 4,111,679 | 9/1978 | Shair et al. | 424/329 |
| 4,225,428 | 9/1980 | Petrovich | 209/166 |
| 4,328,638 | 5/1982 | Smithson | 43/124 |

Primary Examiner—Ivars C. Cintins
Attorney, Agent, or Firm—Raymond M. Speer; R. Brent Olson; William C. Mitchell

[57] ABSTRACT

A method of controlling Corbicula in aqueous systems comprising treating said systems with a cationic polymer. A preferred polymer is a poly (quaternary ammonium) compound having the recurring structure:

[DMDAAX$^\ominus$]

where DMDAAX$^\ominus$ is a polymer unit resulting from monomeric dimethyldiallylammonium X$^\ominus$; and X$^\ominus$ is an anion; said polymer preferably having a weight average molecular weight of from about 200,000 to 400,000.

2 Claims, No Drawings

METHOD OF CONTROLLING CORBICULA

BACKGROUND OF THE INVENTION

1. Field of the Invention

The present invention is concerned with a method of controlling Corbicula, or Asian river clam, in aqueous systems, by utilizing as the molluscicide a cationic polymer.

Particularly, the present invention is concerned with the control of Corbicula in industrial and other cooling water systems by the addition thereto of a molluscicidally effective amount of cationic quaternary ammonium polymer.

On a daily basis, vast quantities of water are removed from rivers, lakes and streams for use in a variety of industrial processes, but the single greatest industrial use of water is for cooling purposes, and the greatest nonconsumptive industrial demand for water as a heat transfer medium comes from the steam-electric generating industry. This water supports an abundance of biological forms, many of which cannot be removed from process water before it is used. While some of these biological forms may not adversely affect the industrial process involved, the biofouling organism, Corbicula, has become an increasingly severe problem in a number of industrial processes utilizing fresh water, particularly steam plant condenser and service water systems.

Corbicula, commonly called the Asiatic clam because of its origin, is a bivalve mollusc belonging to class Pelecypoda, order Heterodonta, and family Corbiculidae. While there has been some discrepancy in the species classification of Corbicula found within the United States, the general consensus now appears to be that only one species, *Corbicula manilensis,* lives within the confines of the continental United States. Nevertheless, the present invention provides a method of controlling Corbicula, whatever species or variety may be present.

Corbicula was first found in the United States in 1938, and has spread across the country within a relatively short time, reaching tremendous population numbers in many major drainage basins. For some utilities, it has become so serious a pest that equipment availability has been seriously compromised, sometimes dropping below 50% of normal. Corbicula fouling and its attendant problems threatens to affect almost every utility and industrial heat-exchanger facility that draws from communicating bodies of fresh water in the temperate and tropical United States.

Corbicula fouling of such equipment as steam condensers can be extremely troublesome. Small clams find their way easily through cold-water-box intake screens. Once within the condenser, they can lodge at bends, constrictions, or tubesheet faces. There is some uncertainty as to the actual mechanical cause of clogging, whether it is only from new arrivals, or, where water velocity is sufficiently low, from clams which anchor themselves to a tube surface and grow there, progressively blocking more and more of the passage until it is occluded entirely. Whatever the actual mechanism, Corbicula can cause devastating operational and maintenance problems.

Control of Corbicula is not only difficult, but there is no present agreement as to how best to achieve it. Prevention by designing condenser tubing large enough to permit all or most of the adult clam population to pass right through without clogging can sometimes result in uneconomical condenser and auxilliary sizing. Shutting down a unit and mechanically reaming the tubes to remove the clams is effective, but less desirable than on-line control. However, most attempts aimed at controlling the clams while the condenser is operating have either been disappointing or given ambiguous results. Such efforts have been mainly chemical, thermal, and mechanical. The present invention concerns such chemical online control of Corbicula.

2. Brief Description of the Prior Art

Various chemical agents for controlling Corbicula, e.g., chlorine, acrolein, formaldehyde, ozone, and malachite green, have met with no, or only limited success; see Hamm, Power, 25–28, January 1982, and Goss and Cain, *Pollut. Eng. Technol.,* 11–17, 1977, and U.S. Pat. No. 4,328,638.

Simple quaternary ammonium compounds have been used to control fouling by microorganisms as well as molluscs. See, e.g., Nashimura et al., Japan Kokai No. 74 81,535 (1974); Roth, German Offenlegungsschrift No. 2,642,606; Sindery, French Pat. No. 1,460,037; and Vallejo et al., *Science,* 119, 470–472 (April, 1954).

Polyquaternary compounds have been utilized for control of microorganisms, i.e., bacteria, fungi, and algae, but have not been suggested for control of larger organisms, especially molluscs, including Corbicula. See, e.g., U.S. Pat. Nos. 4,113,709 and 4,111,679.

DETAILED DESCRIPTION OF THE INVENTION AND PREFERRED EMBODIMENTS

In accordance with the present invention there is provided a method of controlling Corbicula in aqueous systems, comprising adding to such a system a molluscicidally effective amount of a cationic polymer. It is also an aspect of the present invention to employ as the cationic polymer in such a method of treatment, a poly(quaternary ammonium) compound, and particularly poly(didecyldimethyl ammonium chloride) or a poly(quaternary ammonium) compound having the recurring structure: [DMDAAX$^{\ominus}$], where DMDAAX$^{\ominus}$ is a polymer unit resulting from monomeric dimethyldiallylammonium X$^{\ominus}$, and X$^{\ominus}$ is an anion, said polymer preferably having a weight average molecular weight of from about 200,000 to 400,000.

In accordance with the present invention there is also provided a method of controlling Corbicula in industrial and other cooling water systems, comprising adding to such a system a molluscicidally effective amount of a cationic polymer. It is also an aspect of the present invention to employ as the cationic polymer in such a method of treatment, a poly(quaternary ammonium) compound, and particularly poly(didecyldimethyl ammonium chloride) or a poly(quaternary ammonium) compound having the recurring structure: [DMDAAX$^{\ominus}$], where DMDAAX$^{\ominus}$ is a polymer unit resulting from monomeric dimethyldiallylammonium X$^{\ominus}$, and X$^{\ominus}$ is an anion, said polymer preferably having a weight average molecular weight of from about 200,000 to 400,000.

The expression "controlling Corbicula" as used herein is intended to cover killing, inhibiting the growth of, or preventing the growth of, Corbicula. In a similar manner, the expression "molluscicidally effective amount" as used herein means an amount which kills, inhibits the growth of, or prevents the growth of, Corbicula, in the aqueous systems where the molluscicide is employed.

The molluscicidally effective amount of cationic polymer employed in the methods of treatment of the present invention are somewhat variable since they may be influenced by such factors as the ambient temperature of the aqueous system being treated, the presence of substances in the water which bind to or otherwise inactivate the cationic polymer, the concentration and predominant stage of life cycle of the Corbicula present in the aqueous system to be controlled, the particular cationic polymer which is employed and other factors. Generally, however, the molluscicidally effective amount will be in the range of from 1 to 200 parts per million, preferably 2 to 100, most preferably 5 to 50 parts per million, based on the total weight of the aqueous system being treated.

The cationic polymer employed in the methods of treatment of the present invention can be added to the aqueous system being treated in a conventional manner and at any point best suited to provide ready dissolution and rapid distribution of the polymer to all points in the aqueous system being treated. Various formulations of the cationic polymer which facilitate its dissolution in water may be prepared in accordance with known methods.

The methods of treatment of the present invention will be better understood by the following example which illustrates the use of a preferred cationic polymer in controlling Corbicula.

EXAMPLE

Various concentrations of poly(dimethyldiallylammonium chloride) were established in beakers containing 200 ml of Ohio River water. To each beaker was then added six adult *Corbicula manilensis*, as well as to a control beaker containing only river water. Only clams which were definitely alive (feeding) were used in the test. The clams were observed daily for signs of life and the results obtained are set forth in the table below.

| | | Number of Live Clams per Concentration | | | | | | | | |
|---|---|---|---|---|---|---|---|---|---|---|
| Hours | Control | 0.1 mg/l | 0.2 mg/l | 0.5 mg/l | 1.0 mg/l | 2.0 mg/l | 5.0 mg/l | 10.0 mg/l | 25 mg/l | 100 mg |
| 2 | 6 | 6 | 6 | 6 | 6 | 6 | 6 | 6 | 6 | 6 |
| 18 | 6 | 6 | 6 | 6 | 6 | 6 | 6 | 6 | 6 | 6 |
| 41 | 6 | 6 | 6 | 6 | 6 | 6 | 6 | 5 | 6 | 5 |
| 69 | 6 | 6 | 6 | 6 | 6 | 6 | 6 | 5 | 5 | 5 |
| 144 | 6 | 6 | 6 | 6 | 6 | 6 | 6 | 2 | 0 | 0 |
| 165 | 6 | 6 | 6 | 6 | 6 | 6 | 4 | 1 | 0 | 0 |
| 189 | 6 | 6 | 6 | 6 | 6 | 6 | 4 | 1 | 0 | 0 |
| 210 | 6 | 6 | 6 | 6 | 6 | 6 | 4 | 0 | 0 | 0 |

What is claimed is:

1. A method of controlling Corbicula in aqueous systems used for cooling or service water purposes, comprising adding to such a system a molluscicidally effective amount of poly(dimethyldiallyl ammonium chloride), wherein said poly(dimethyldiallyl ammonium chloride) has a weight average molecular weight of from about 200,000 to 400,000.

2. The method of claim 1, wherein 1 to 200 ppm of poly(dimethyldiallyl ammonium chloride) is used.

* * * * *